United States Patent
Garcia

(10) Patent No.: US 10,206,935 B1
(45) Date of Patent: Feb. 19, 2019

(54) CREAM THAT TREATS PODODERMATITIS

(71) Applicant: Griselle J Garcia, Hialeah, FL (US)

(72) Inventor: Griselle J Garcia, Hialeah, FL (US)

(*) Notice: Subject to any disclaimer, the term of this patent is extended or adjusted under 35 U.S.C. 154(b) by 0 days.

(21) Appl. No.: 16/010,133

(22) Filed: Jun. 15, 2018

(51) Int. Cl.
| | | |
|---|---|---|
| *A61K 31/325* | (2006.01) | |
| *A61K 31/573* | (2006.01) | |
| *A61K 31/7036* | (2006.01) | |
| *A61K 33/04* | (2006.01) | |
| *A61K 38/12* | (2006.01) | |
| *A61K 31/265* | (2006.01) | |
| *A61K 31/702* | (2006.01) | |

(52) U.S. Cl.
CPC .......... *A61K 31/573* (2013.01); *A61K 31/265* (2013.01); *A61K 31/325* (2013.01); *A61K 31/702* (2013.01); *A61K 31/7036* (2013.01); *A61K 33/04* (2013.01); *A61K 38/12* (2013.01)

(58) Field of Classification Search
CPC ................ A61K 31/325; A61K 31/573; A61K 31/7036; A61K 33/04; A61K 38/12
See application file for complete search history.

(56) References Cited

U.S. PATENT DOCUMENTS

| | | | | |
|---|---|---|---|---|
| 5,766,579 A | * | 6/1998 | Earles ..................... | A61K 8/23 424/401 |
| 8,613,961 B1 | * | 12/2013 | Filippova ............... | A01N 65/00 424/401 |
| 2007/0184124 A1 | * | 8/2007 | Harlan ..................... | A61K 8/23 424/703 |
| 2014/0030314 A1 | * | 1/2014 | Larson ................. | A61K 31/327 424/443 |

OTHER PUBLICATIONS

Ermis Labs. Medicated Bars by Ermis Labs Launched at American Academy of Dermatology Summer Meeting. PRWeb Newswire. Aug. 27, 2014. (Year: 2014).*

* cited by examiner

*Primary Examiner* — Jeffrey E. Russel
(74) *Attorney, Agent, or Firm* — Ruben Alcoba, Esq.

(57) ABSTRACT

This application is directed to cream that treats canine pododermatitis that is caused by a bacterial infection. The cream is composed of a Sulfur mineral powder, a Hydrocortisone cream, a Tolnaftate cream and a triple antibiotic cream. The cream is applied to the affected areas of the dog's paws 2-3 times daily for a period of at least two weeks.

5 Claims, No Drawings

CREAM THAT TREATS PODODERMATITIS

BACKGROUND

The present invention is a cream that treats pododermatitis that is caused by a bacterial infection. Pododermatitis is an inflammation that can be caused by many disorders including infections, allergies, hormonal disorders, immune-mediated diseases, tumors or cancers and environmental contaminants.

The inventor of the present invention is a dog owner and invented the present cream due to a condition that affected two of her dogs, pododermatitis. One dog died without being cured and the second dog was cured by the cream that she invented.

Pododermatitis is defined as inflammation of the skin of the paw. Affected tissues may include interdigital spaces, footpads, nail folds (paronychia), and nails.

Her first dog developed pododermatitis in between the openings of his paws. The dog was taken to the veterinarian on repeated basis and was treated for the ailment. The dog eventually built a resistance to the creams and drugs he was being treated with and died with the ailment.

Her first dog was treated with liquid antibiotics that would improve the dogs condition on a temporary basis, yet the antibiotics never cured the condition. The condition crippled her dog and caused much mental anxiety amongst her family, for they all had to witness the dogs suffering.

After her first dog passed, she acquired a second dog. Her second dog also developed the condition. This dogs condition was very similar to her first dogs. The dog developed cysts between the openings of his paws that filled with blood and puss.

A specimen was taken from the dog's paws and it was found that he suffered from a bacterial infection that led to the condition. The dog condition was repeatedly treated with antibiotics. The antibiotics did not cure the condition for it appeared that the bacteria he was being treated for was resistant to the antibiotics.

The futility of the treatment inspired her to seek or invent a treatment that would cure her dog. She read many articles and studies that led her to develop the present cream/formula for the treatment of her dog.

The cream she invented allowed her dog to be cured within two weeks and the condition has not returned. She knows that the combination of sulfur with the other compounds/creams discussed in this presentation cured her dogs condition.

For the foregoing reasons there is a need for a cream that treats pododermatitis that is caused by a bacterial infection.

SUMMARY

The present invention is a cream that treats canine pododermatitis that is caused by a bacterial infection. The invention is a cream that comprises of a Sulfur mineral powder, a Hydrocortisone cream, a Tolnaftate cream and a triple antibiotic cream.

The cream is applied to the affected areas of the dog's paws 2-3 times daily for a period of at least two weeks.

An object of the present invention is to provide a cream that will treat pododermatitis that is caused by bacterial infection.

Another object of the present invention is to provide a cream that will improve the health of a dog.

DESCRIPTION

The present invention is a cream that treats dogs whom suffer from pododermatitis that is caused by a bacterial infection. The cream comprises of A Sulfur mineral powder, a Hydrocortisone cream, a Tolnaftate cream, and a triple antibiotic cream.

The inventor, through trial and error, composed her cream based on the weight of each component needed for the cream. The cream that cured her dog was comprised of the following components in the stated weights: the weight of the Sulfur mineral powder is 5.6 grams, the weight of the Hydrocortisone cream is 3.7 grams, the weight of the Tolnaftate cream is 3.9 grams, and the weight of the Triple antibiotic cream is 2.8 grams.

The Triple antibiotic cream of the present invention is made using the following three antibiotics: a Bacitracin; a Neomycin; and a Polymyxin B, and each gram of the Triple antibiotic cream consists of 5.41 mg of Bacitracin, 3.5 mg of Neomycin; and 0.6 mg of Polymyxin B.

By extrapolating the weight of the components, the inventor knows that the percentage of each component of her cream, by percentage, is as follows: the Sulfur mineral powder is 35% of the cream; the Hydrocortisone cream is 23.12% of the pododermatitis cream; the Tolnaftate cream is 24.38% of the pododermatitis cream; and the Triple antibiotic cream is 17.50% of the pododermatitis cream.

The Tolnaftate component used in the present invention is a Tolnaftate 1% cream.

The inventor recommends giving the canine being treated between 500 to 100 mg of Cod Oil, daily, during the treatment.

An advantage of the present invention is that it provides a cream that treats pododermatitis that is caused by bacterial infection.

Another advantage of the present invention is that it provides a cream that improves the health of a dog.

While the inventor's above description contains many specificities, these should not be construed as limitations on the scope, but rather as an exemplification of several preferred embodiments thereof. Many other variations are possible. Accordingly, the scope should be determined not by the embodiments illustrated, but by the appended claims and their legal equivalents.

What is claimed is:

1. A cream that treats pododermatitis caused by bacterial infections, the cream comprising:
   A Sulfur mineral powder;
   A Hydrocortisone cream;
   A Tolnaftate cream; and
   A Triple antibiotic cream.

2. The cream that treats pododermatitis caused by bacterial infections of claim 1, wherein the weight of the Sulfur mineral powder is 5.6 grams, the weight of the Hydrocortisone cream is 3.7 grams, the weight of the Tolnaftate cream is 3.9 grams, and the weight of the Triple antibiotic cream is 2.8 grams.

3. The cream that treats pododermatitis caused by bacterial infections of claim 2, wherein the Sulfur mineral powder is 35% of the pododermatitis cream, the Hydrocortisone cream is 23.12% of the pododermatitis cream, the Tolnaftate cream is 24.38% of the pododermatitis cream, and the Triple antibiotic cream is 17.50% of the pododermatitis cream.

4. The cream that treats pododermatitis caused by bacterial infections of claim 3, wherein each gram of the Triple antibiotic cream comprises of 5.41 mg of Bacitracin, 3.5 mg of Neomycin, and 0.6 mg of Polymyxin B.

5. The cream that treats pododermatitis caused by bacterial infections of claim 4, wherein the Tolnaftate cream is 1% w/w Tolnaftate cream.

\* \* \* \* \*